United States Patent [19]

Smit et al.

[11] 4,204,110
[45] May 20, 1980

[54] DECORATIVE PERSONAL ELECTRIC HEATING APPLIANCE

[76] Inventors: Helen E. Smit; Julie A. Smit, both of 1045 Hinman Ave., Evanston, Ill. 60202

[21] Appl. No.: 774,958

[22] Filed: Mar. 7, 1977

[51] Int. Cl.² .......................... H05B 1/00; A61F 7/04
[52] U.S. Cl. .......................................... 219/313; 46/88; 46/116; 128/258; 128/399; 150/2.1; 215/217; 215/356; 219/201; 219/522; 219/528
[58] Field of Search .............. 219/341, 300, 201, 528, 219/529, 211, 212, 522; 119/1; 5/284; 116/114 V; 46/45, 87, 88, 156, 158, 115, 116; 128/1 C, 24.1, 82.1, 258, 399–403; 150/2.1–2.7, 52 E; 215/217, 356, 357; 126/263, 204; 220/3.1

[56] References Cited

U.S. PATENT DOCUMENTS

| | | | |
|---|---|---|---|
| 543,177 | 7/1895 | Daly | 150/2.6 |
| 853,639 | 5/1907 | Hincks | 150/2.1 |
| 879,516 | 2/1908 | Cantwell | 150/2.2 X |
| 1,346,176 | 7/1920 | Chambers | 150/2.1 |
| 1,540,984 | 6/1925 | Fraternali | 220/3.1 X |
| 1,558,278 | 10/1925 | Phillips | 150/2.1 |
| 1,819,913 | 8/1931 | Miller et al. | 128/258 UX |
| 1,896,663 | 2/1933 | Collins | 46/116 X |
| 2,285,776 | 6/1942 | Malloy | 219/313 |
| 2,294,010 | 8/1942 | Van Daam | 219/313 |
| 3,125,984 | 3/1964 | Okuyama | 116/114 V |
| 3,523,848 | 8/1970 | Huff et al. | 150/2.1 |
| 3,634,655 | 1/1972 | Jordan | 219/528 X |

FOREIGN PATENT DOCUMENTS

| | | | |
|---|---|---|---|
| 753955 | 3/1967 | Canada | 215/217 |
| 376885 | 11/1921 | Fed. Rep. of Germany | 219/313 |
| 483178 | 7/1953 | Italy | 150/2.1 |
| 409306 | 4/1934 | United Kingdom | 219/313 |
| 508886 | 7/1939 | United Kingdom | 150/2.1 |
| 652572 | 4/1951 | United Kingdom | 150/2.1 |

Primary Examiner—A. Bartis
Attorney, Agent, or Firm—Laff, Whitesel & Rockman

[57] ABSTRACT

A decorative personal electric heating appliance has an exterior covering in the form of a stuffed animal, doll, novelty item, etc. having a predetermined appearance, texture or feel which is psychologically attractive and cuddly. The exterior covering encloses an internal fluid-containing bladder having a fill opening. An electric immersion heater means is provided in the bladder for heating the fluid. The stopper for the bladder fill opening and the electrical connector for the electric heater are located recesses in the exterior covering covered by childproof caps camouflaged to blend in with the exterior covering. A temperature indicator is provided on the exterior covering to indicate the temperature of the appliance. The bladder may be emptied and refilled with a cold medium to enable the appliance to be used for cooling if desired.

13 Claims, 6 Drawing Figures

DECORATIVE PERSONAL ELECTRIC HEATING APPLIANCE

This invention relates to heated or cooled objects and more particularly to novelty, toy and display items, especially well adapted for heating or cooling the skin of a person.

There are many times when a temperature controlled object is necessary or desirable and when the psychological responses to the object may be its most important aspects. An important example of the usage of a heated object is a toy for an infant to clutch. Psychologically this would be extremely beneficial for newborn infants. Another example is children having trouble falling asleep, could be greatly comforted by these warm, cuddly animals and shapes, relaxing them and enabling them to fall into an easy sleep. It would give a warm, secure feeling to children. A parental substitute, warm, cuddly, furry body is as important to the child as the heat, per se.

Another example of the usage of this temperature controlled object might be as a cooling device, and filled with ice and cold water or a cooling chemical. On hot, humid days a cool toy would be desirable for the child. Since the embodiment would be a toy, it could be taken in a car, to a beach, on shopping trips, and the like to cool the child, making him more comfortable while away from home. For any of these or similar usage, the appearance, texture, and feel of the object plus the heating or cooling features are very important aspects of the invention. This invention is for the use of all children, including sick and well children, teenagers, and also adults—according to the usage and the decorative design of the device.

Accordingly, an object of the invention is to provide temperature controlled objects having psychological connotations. Here, an object is to provide a part time substitute which could represent a mother to very small infants and infant-children. In this connection, an object is to provide safe devices for persons who are not competent to care for themselves.

Another object of the invention is to provide structures of the described types which are suitable for both heat and cold.

Yet another object of the invention is to provide a psychological "crutch" in the general class of security blankets, pacifiers and the like.

In keeping with an aspect of the invention, these and other objects are accomplished by providing a device having a predetermined appearance, texture, or feel. Preferably, the device may be filled with water or a chemical having a substantial thermal inertia. The water or chemical is heated or cooled to give the desired temperature characteristics. Safety features are built into the device to prevent the person from being injured by its use.

The nature of preferred embodiments of the invention may become more apparent from the attached drawings wherein:

FIG. 5 is a schematic view of a thermostat-controlled cable system for automatically heating a plurality of the devices, for use in a hospital, nursery or the like.

Figure 1:
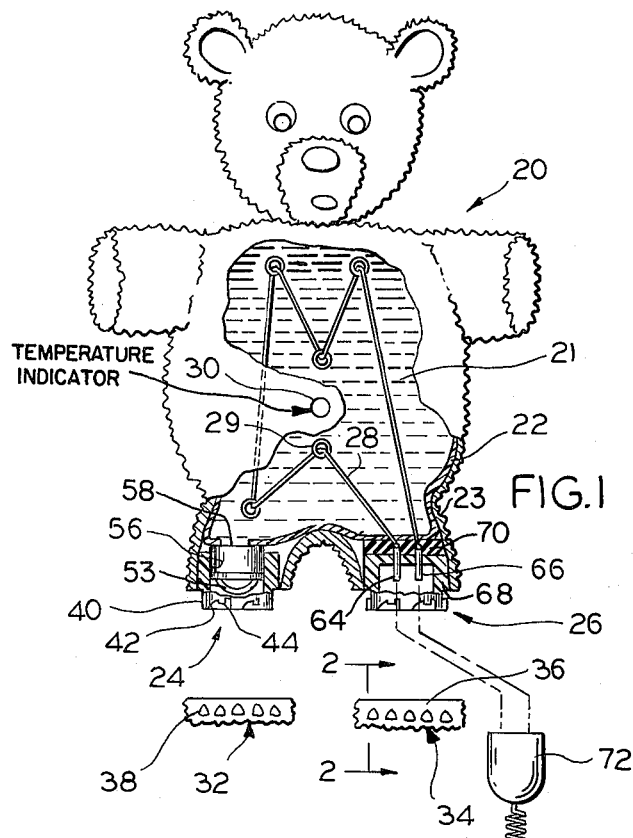
FIG. 1 is a pictorial representation partially in section of an exemplary teddy bear incorporating the invention.
Figure 2:
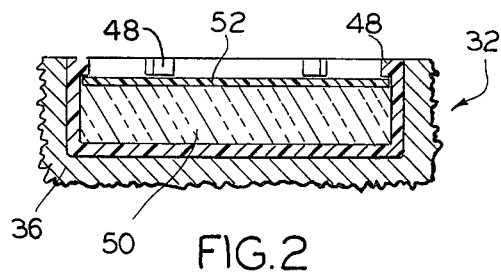
FIG. 2 is a cross-sectional view of an exemplary "child-proof" cap for sealing entrances to the device.

FIG. 1 shows a personal appliance in the form of a teddy bear 20, which represents any suitable texture, appearance or feel that may appeal to infants and children. Usually, this device will have the appearance of the stuffed animal or animals which is of current popularity, and which has proven appeal to infants and children. Normally such animals have a generally fur-like feel and, therefore, the appliance may be covered with a fur-like material 23.

Inside the device, there is a large cavity 21 defined by the internal walls of a preferably molded bladder 22 for receiving and containing any suitable material having a substantial thermal inertia, such as water or another liquid or a gel. The bladder 22 (which may be made of a non-toxic, silicone rubber, for example) preferably terminates at opening 24 which give access to the interior thereof. Opening 24 has a removable stopper which gives access for purposes of filling or emptying the bladder. Outlet 26 has electrical connections for enabling power to be supplied to an internal heating element 28. Preferably, the opening 24 and outlet 26 are located on the end of a limb or elsewhere in positions which may be completely covered by a cap which has the same appearance as the animal. This way, it does not detract from the overall appearance and does not attract the attention of a child who might be tempted to play with the cap and possibly spill hot water over himself.

The heating element 28 is widely supported at a plurality of points shown here as rings 29, in order to provide a good heat distribution pattern. Rings 29 are secured to the inner bladder walls 22. This step could be performed during the molding process of bladder 22 or at a later time with a suitable cement.

At some point appropriate to the decorative effects of the teddy bear, there is a heat responsive temperature indicator 30 which changes its color responsive to the temperature surrounding it. This temperature indicator 30 may be a crystal which changes its color as a function of its temperature. Therefore, the heat at the surface of the teddy bear may be easily ascertained by a visual inspection of temperature indicator 30.

Suitable "child proof" caps 32, 34 are provided for sealing the opening 24 and outlet 26 without disturbing either the appearance or the feel of the device. In greater detail, each cap is here shown as having an exterior "fur" or other material 36 which matches the fur-like material 23 covering the body of the animal. Even the toes 38 may be supplied to heighten the appeal of the animal-like appearance.

Capture slots are provided on the part 40 of the coupling which projects outwardly from the body 22. For example, as here shown, each capture slot comprises an inclined ramp 42 leading to an indentation 44. The mating part of the cap 32 includes a plurality of inwardly projecting ears 48 which are shaped and proportioned to fall into the capture indentations 44. A pad of resilient and compressible material 50 pushes a wear resistant disc 52 outwardly. Therefore, to install the cap, it is only necessary to place it over part 40 and rotate, the ears 48 climb the inclined ramps, as at 42, and the ears are then pushed into the capture indentations 44 by the compression of the resilient pad 50. To remove the cap, it is only necessary to push it in, thereby compressing the resilient material 50 and moving the ears out of the capture indentations 44. At that time, the cap may be rotated in a reverse direction to free the ears.

Figure 4:
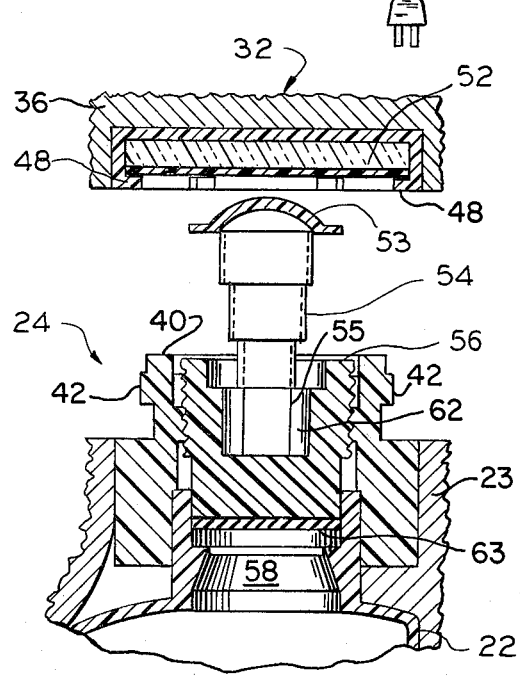
FIG. 4 is a cross-sectional view of a removable stopper for a fill opening for the device.

The removable stopper at 24 is better seen in FIG. 4. Preferably, there is a rectangular, telescoping section 54 which may be manually pulled outwardly from its compact position within space 62 by a small loop 53 (as shown in FIG. 4) and then section 54 is turned. The resulting rotational forces unscrew a plug 56 to which the bottom telescoping section 55 is permanently attached, with a washer on bottom 63 which opens a spout 58, so that bladder 22 may be emptied or filled when necessary. The fluid will ordinarily be left in the bladder to keep its shape. After the plug 56 is screwed back into the spout 58, the telescoping section 54 may be pushed into space 62 in order to provide a compact filling device that may be covered by the cap 32.

When the telescoping handle 54 is in its compact position within space 62, each narrower section is contained within its neighboring wider section, thereby giving the appearance of no handle on the removable stopper 56. An advantage of this type of removable stopper and telescoping handle under a child-proof cap is that it cannot easily be opened by small children.

Figure 3:
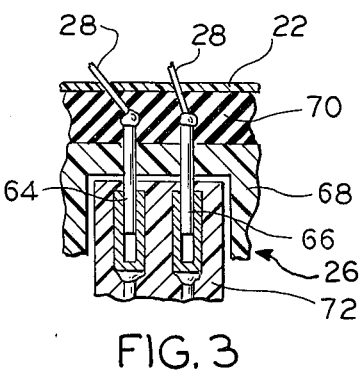
FIG. 3 is a cross-sectional view of a plug and a jack which may be used to make electrical connections with the inventive device.

FIG. 3 shows the construction of the electrical connections of outlet 26 wherein a pair of terminals 64, 66 are soldered or otherwise connected to wires 28. Terminals 64, 66 are preferably molded into a socket 68, to form a jack, which is sealed to bladder 22 by a suitable potting compound 70, in order to make a secure, rigid and waterproof seal. This jack provides a connection to a power line (not shown) via a separate electrical cord which is terminated by a plug 72 on one end. This electrical cord could be self-compressing when freed from an outside outlet and socket 68 on the appliance. It would compress into a coiled shape when not in use and, therefore, require no manual folding or unfolding after and before usage.

For use in large nurseries or hospitals, a plurality of such plugs 72 may be connected to a power line via a temperature control unit 74 to permit a plurality of animals 20 to be simultaneously heated. Each plug 72 may be connected to a different stuffed animal. These plugs are used only during heating. After the animal is heated, the plugs are removed and the animal is returned to the state seen in FIG. 1, before being given to the child. Preferably, a single thermostat 76 may be placed within the opening 24 of one of the stuffed animals to signal temperature control unit 74 when the water in that stuffed animal has reached a desired temperature. The cap 78 of thermostat 76 is substituted directly for the cap 32 and plug 56 during heating. The thermostat 76 extends into the bladder 22 through spout 58 to sense the temperature of the fluid therein. After the animal 20 with the thermostat 76 is properly heated, the thermostat 76 is removed and then the plug 56 and cap 32 replaced whereby opening 24 is sealed in a child-proof manner. The plugs 72 are detached from the animals 20 and the outlet 26 of each animal covered by caps 34. Operability of the arrangement shown in FIG. 5 is predicated on the assumption that, if the one animal 20 which receives the thermostat 76 is heated to the proper temperature, all of the other animals 20 energized from the control unit 74 through plugs 72 will also have approximately the same temperature.

Figure 5:
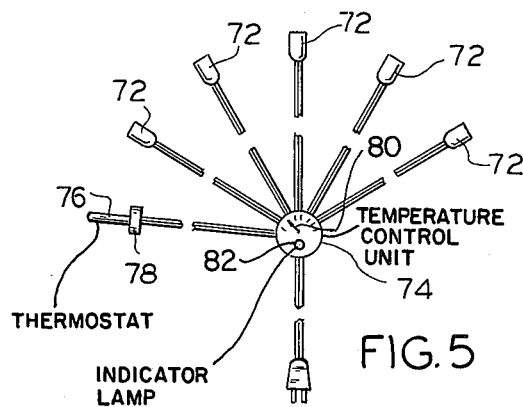

FIG. 5 has been drawn to show that any suitable temperature may be selected at 80 and that a light 82 may light to signal when the desired temperature has been reached.

Figure 6:
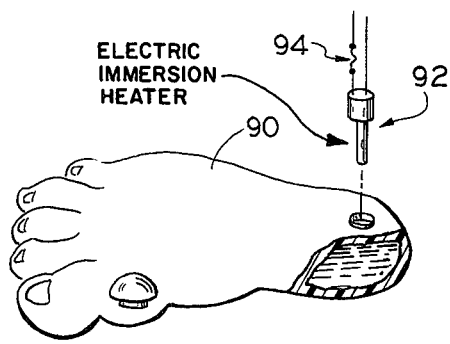
FIG. 6 is a pictorial view of an alternative device having a different appearance, texture and feel.

The foregoing description has been directed to a child's appliance. However, the invention has equal applicability to appliances for adults. More particular, FIG. 6 shows a similar appliance 90 having any suitable appearance. Here, it is thought that a humorous approach might be in the nature of a human foot with a bunyon covering the cap for someone who has a headache or hangover and feels as if he were "kicked in the head". Here the foot is a soft sponge rubber, dense foam, or the like. The idea is to give the structure a texture and feel of human skin.

Other approaches to our decorative personal heated and cooled appliance might include almost any shape from pillows through hearts and flowers to psychedelic free forms. A device such as a warm decorative pillow or a heated back rest or a temperature-controlled footrest would be very comforting to adults and also to aged adults. These embodiments would all have a decorative exterior covering over a bladder with an empty/fill opening and an electrical connection therein. These openings would be situated in an appropriate location on the appliance.

For most appliances, it is preferable to have a device which is heated before it is used, so that the person using the device will not come into contact with live power cords. This is especially important for the stuffed animal used by small children.

However, when the appliance is used by an adult, who wants to use it over extended periods of time, an electric immersion heating element 92 may be used. This heater 92 is similar to devices used to heat aquariums, especially those for tropical fish. A fuse 94 may be provided to burn out and open the heating circuit before a dangerous temperature is reached. The heater may simply be inserted into the appliance through an opening therein such as shown at 96 in FIG. 6.

During hot weather, it may be desirable to pour out the water and to fill the bladder 22 with cold water and ice cubes. This could be done by removing safety cap 32 and removable stopper 56 and putting ice cubes, or cold water, directly into the empty/fill opening 24 to cool the bladder 22.

This invention is to include (heated or cooled): stuffed animals, dolls, and novelty items such as a "Big Foot", heated decorative pillows, warmed back rests, and temperature controlled foot rests. Those who are skilled in the art will readily perceive how the invention may be modified. Therefore, the appended claims are to be construed to cover all equivalent structures falling within the scope and spirit of the invention.

We claim:

1. A decorative personal heating appliance comprising means defining a decorative exterior covering enclosing an internal fluid-containing bladder having a fill opening therein, electric heater means inside said bladder for heating the fluid contained therein, electrical connector means associated with said electric heater means and extending from said bladder means into a first open recess in said decorative covering for enabling an external power source to be connected to said heater means, whereby said power source may be disconnected from said heater means while said appliance is in use, detachable electrical connection means for applying energy from an external power source via said connector means to said heater means, means comprising a removable stopper for controlling said opening and for enabling a filling or emptying of said bladder via said opening, said opening and stopper being positioned in a second open recess in said decorative exterior covering, and removable child-proof cap means camouflaged to blend in with said exterior covering for closing each of said open recesses for concealing said stopper means and said connector means.

2. The appliance of claim 1 wherein said exterior covering is in the form of a stuffed animal.

3. The appliance of claim 1 wherein said exterior covering is in the form of a predetermined decorative shape, selected from the group of stuffed animals, dolls, novelty items, pillows, back and foot rests.

4. The appliance of claim 3 and heat-responsive, temperature indicator means on the exterior of said covering for indicating the surface temperature of the appliance.

5. The appliance of claim 4 wherein said heat-responsive, temperature indicator means is a material which changes color at a predetermined temperature.

6. The appliance of claim 1 wherein said removable stopper has a telescoping handle means for selectively manipulating said stopper, the handle means collapsing to a compact storage position when said opening is sealed, whereby said handle means may be extended, said bladder may be opened or sealed, and then the handle means may be collapsed to a compact and closed position.

7. The appliance of claim 1 and distribution means for simultaneously applying energy to a plurality of said appliances, and distribution means including a temperature control device receivable in said fill opening of one of said plurality of said appliances in lieu of the removable stopper, and means responsive to said temperature control device for indicating when the temperature in said one of said devices reaches a predetermined temperature.

8. The appliance of claim 1 wherein said decorative exterior covering includes at least some simulation of fur.

9. The appliance of claim 1 wherein said decorative exterior covering includes at least some simulation of skin.

10. The appliance of claim 1 wherein said heater means is an electric immersion heating unit.

11. A decorative personal heating appliance comprising a decorative and animal-simulating exterior covering in combination with an electric heater means for heating said appliance to a predetermined temperature, non-removable fluid-containing bladder means inside said animal-simulating exterior covering for containing a fluid, said fluid-containing bladder having a fill opening and the fluid in said bladder being heated by said electrical heater means to a desired temperature, said appliance being capable of being disconnected from the electrical current during its use, said fill opening being closed by a removable stopper, said fill opening and stopper being located in a first recess in said exterior covering, said first recess having a rim around it to which a cap may be attached to conceal said fill opening and stopper, an electrical connector means associated with said heater means for enabling an external power source to be connected to said heater means, said connector means being within a second recess in the exterior covering of said appliance, said second recess having a rim around it to which a cap may be attached to conceal said electrical connector means, said electrical connector means and heater means being permanently attached to said appliance whereby they cannot be removed from said appliance, said heater means being functionable when connected to said external power source regardless of appliance's position while being energized, removable cap means fitting onto the rims of said recesses, said cap means continuing said animal-simulating exterior covering of said appliance for camouflaging the recesses to conceal the fill opening and stopper and connector means, and said bladder being capable of being drained of fluid through said fill opening and being refilled with a cold medium.

12. A decorative personal heating appliance comprising means defining a decorative animal-simulating exterior covering enclosing an internal fluid-containing bladder having a fill opening therein, said fill opening being located in an open recess in the exterior covering of said appliance, said bladder being non-removable from said exterior covering, electrical heater means inside said bladder for heating a fluid contained therein, electrical connector means located within an open recess in said exterior covering and associated with said heater means for enabling an external power source to be connected to said heater means, whereby said power source may be disconnected from said heater means while said appliance is in use, detachable connector means for applying energy to said heater means via said connector means associated with said heater means, means comprising a removable stopper for controlling said fill opening and for enabling the filling or emptying of said bladder via said opening, and removable cap means camouflaged to blend in with said animal-simulating exterior covering for covering said open recesses and concealing said stopper and said connector means.

13. A decorative personal heating appliance comprising means defining a decorative exterior covering, said exterior covering being in a form selected from the group of stuffed animals, dolls, novelty items, pillows, and back- and footrests, heat-responsive, temperature indicator means on the exterior of said covering for indicating the surface temperature of the appliance, said heat-responsive means being a material which changes color at a predetermined temperature, said exterior covering enclosing an internal fluid-containing bladder having a fill opening formed therein, electric heater means inside said bladder for heating a fluid contained therein, said heater means being an immersion heating means for heating the fluid in said bladder a predetermined temperature, said bladder being filled or emptied via said fill opening, electrical connector means associated with said heater means for enabling an external power source to be connected to said heater, whereby said power source may be disconnected from said heater means while said appliance is in use, detachable electrical connection means connectable to a source of electric power for applying energy via said connector means to said heater means, means comprising a removable stopper for controlling said opening for filling or emptying said bladder via said opening, said removable stopper having a telescoping handle means for selectively manipulating said stopper, the handle means collapsing into a compact storage position within said appliance when said opening is sealed, whereby said handle means may be extended, said appliance may be opened or sealed, and then the handle means may be collapsed to a compact and closed position, child-proof cap means camouflaged to blend in with said exterior covering for concealing and stopper means and said connector means, said exterior covering including a pair of open recesses, the fill opening and stopper being positioned in and accessible through one of the recesses and the connector means being positioned in and accessible through the other recess and the child-proof cap means covering the respective recesses to conceal said stopper and connector means.

* * * * *